US012594117B2

(12) United States Patent　　　　(10) Patent No.:　US 12,594,117 B2
Jensrud et al.　　　　　　　　　　　(45) **Date of Patent:　　*Apr. 7, 2026**

(54) MEDICAL SYSTEMS, DEVICES, AND RELATED METHODS

(71) Applicant: Boston Scientific Scimed, Inc., Maple Grove, MN (US)

(72) Inventors: Allyn Jensrud, Milford, MA (US); Mingxiang Xu, Wayland, MA (US); Matthew Jones, Shoreview, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 645 days.

This patent is subject to a terminal disclaimer.

(21) Appl. No.: 18/145,591

(22) Filed: Dec. 22, 2022

(65) Prior Publication Data

US 2023/0128015 A1　　Apr. 27, 2023

Related U.S. Application Data

(63) Continuation of application No. 16/861,557, filed on Apr. 29, 2020, now Pat. No. 11,564,739.

(Continued)

(51) Int. Cl.
　*A61B 18/14*　　　(2006.01)
　*A61B 18/00*　　　(2006.01)
　*A61B 18/16*　　　(2006.01)

(52) U.S. Cl.
　CPC .................... *A61B 18/1492* (2013.01); *A61B 2018/00029* (2013.01); *A61B 2018/00178* (2013.01);

(Continued)

(58) Field of Classification Search
　CPC ...... A61B 18/1492; A61B 2018/00178; A61B 2018/0091; A61B 2018/1475;

(Continued)

(56) References Cited

U.S. PATENT DOCUMENTS 4,682,596 A　*　7/1987　Bales ................. A61B 18/1492
　　　　　　　　　　　　　　　　　　　　606/45
6,193,717 B1　*　2/2001　Ouchi ................ A61B 18/1477
　　　　　　　　　　　　　　　　　　　　606/49

(Continued)

FOREIGN PATENT DOCUMENTS

CN　　　　　1817318 A　　　8/2006
CN　　　　103860264 A　　　6/2014

(Continued)

OTHER PUBLICATIONS

Office Action in Japanese Application No. 2021-565719, dated Jan. 16, 2024 (7 pages).

(Continued)

*Primary Examiner* — Jaymi E Della
(74) *Attorney, Agent, or Firm* — Bookoff McAndrews PLLC

(57)　　　　　　　　ABSTRACT

A medical device includes a shaft including a distal end including a passive electrode that defines a central opening extending through the passive electrode, and an active electrode within the central opening. The active electrode is movable between at least an extended position in which the active electrode does not contact the passive electrode, and a retracted position in which the active electrode contacts the passive electrode.

18 Claims, 4 Drawing Sheets

Related U.S. Application Data

(60) Provisional application No. 62/843,759, filed on May 6, 2019.

(52) U.S. Cl.
CPC ............... *A61B 2018/00196* (2013.01); *A61B 2018/0091* (2013.01); *A61B 2018/1475* (2013.01); *A61B 2018/162* (2013.01); *A61B 2218/002* (2013.01)

(58) Field of Classification Search
CPC ........ A61B 2218/002; A61B 2018/162; A61B 2018/00196

See application file for complete search history.

(56) References Cited

U.S. PATENT DOCUMENTS

| | | | | |
|---|---|---|---|---|
| 2006/0276784 A1* | 12/2006 | Miyajima | .......... | A61B 18/1492 606/46 |
| 2008/0021444 A1* | 1/2008 | Scoption | ................ | A61B 1/018 606/37 |
| 2009/0105739 A1* | 4/2009 | Toyonaga | .......... | A61B 18/1492 606/169 |
| 2013/0317500 A1* | 11/2013 | Scopton | .......... | A61B 17/32056 606/49 |
| 2016/0008063 A1* | 1/2016 | Wake | ................. | A61B 17/3203 606/49 |
| 2016/0220301 A1 | 8/2016 | Yamamoto et al. | | |
| 2017/0209207 A1 | 7/2017 | Devries et al. | | |

FOREIGN PATENT DOCUMENTS

| | | |
|---|---|---|
| CN | 107242902 A | 10/2017 |
| EP | 1728462 A2 | 12/2006 |
| JP | 2004167081 A | 6/2004 |
| JP | 2006326157 A | 12/2006 |
| JP | 2014054372 A | 3/2014 |
| WO | 2014196746 A1 | 12/2014 |
| WO | 2016021230 A1 | 2/2016 |

OTHER PUBLICATIONS

International Search Report and Written Opinion issued in International Application No. PCT/US/2020/030400, issued Nov. 6, 2020 (11 pages).
Office Action in Chinese Application No. 202080034079.3, dated Nov. 10, 2023 (7 pages).

* cited by examiner

400

POSITION A DISTAL PORTION OF A MEDICAL DEVICE
PROXIMATE TO OR WITHIN TISSUE — 402

EXTEND AN ELECTRODE DISTALLY — 404

DELIVER ENERGY TO THE ELECTRODE, AND RESECT
THE TISSUE WITH THE ENERGIZED ELECTRODE — 406

RETRACT THE ELECTRODE PROXIMALLY — 408

DELIVER ENERGY TO THE ELECTRODE, AND CAUTERIZE
THE TISSUE WITH THE ENERGIZED ELECTRODE — 410

MEDICAL SYSTEMS, DEVICES, AND RELATED METHODS

CROSS-REFERENCE TO RELATED APPLICATION(S)

This application is a continuation of U.S. Application Ser. No. 16/861,557, filed on Apr. 29, 2020, now U.S. Pat. No. 11,564,739, issued Jan. 13, 2023, which claims the benefit of priority from U.S. Provisional Application No. 62/843,759, filed on May 6, 2019, each of which is incorporated by reference herein in its entirety.

TECHNICAL FIELD

Aspects of the present disclosure generally relate to medical systems, devices, and methods. In particular, aspects of the present disclosure relate to medical systems, devices, and procedures for treating tissue by delivering electrical energy to tissue.

BACKGROUND

Medical devices, such as endoscopes or other suitable insertion devices, are employed for a variety of types of diagnostic and surgical procedures, such as endoscopy, laparoscopy, arthroscopy, gynoscopy, thoracoscopy, cystoscopy, etc. Many of these procedures involve delivering energy to tissue of an organ or a gland to treat tumors, infections, and the like. Examples of such procedures include Endoscopic Mucosal Resection (EMR), Endoscopic Sub-mucosal Resection (ESR), Endoscopic Sub-mucosal Dissection (ESD), polypectomy, mucosectomy, etc. In particular, such procedures may be carried out by inserting an insertion device into a subject's body through a surgical incision, or via a natural anatomical orifice (e.g., mouth, vagina, or rectum), and performing the procedure or operation at a target site with an auxiliary device inserted through the insertion device.

At times, during a medical procedure, a user may use an injection needle inserted through an insertion device to form (or re-form) a bleb in or under tissue to be removed. In order to deliver energy to the tissue, the user may be required to remove the injection needle from the insertion device and deliver an energy delivery device through the insertion device to the tissue being targeted. Additionally, during the procedure, the user may provide hemostasis to the tissue being targeted or surrounding tissue. The exchange of devices may increase the duration and risks of the medical procedure, and the energy delivery device may not provide adequate energy delivery in both a cutting mode and a hemostasis mode.

The devices and methods of the current disclosure may rectify some of the deficiencies described above or address other aspects of the prior art.

SUMMARY

Examples of the present disclosure relate to, among other things, medical devices for treating tissue by delivering electrical energy to the tissue and related methods of use thereof. Each of the examples disclosed herein may include one or more of the features described in connection with any of the other disclosed examples.

In one example, a medical device may include a shaft including a distal end including a passive electrode that defines a central opening extending through the passive electrode, and an active electrode within the central opening. The active electrode may be movable between at least an extended position in which the active electrode does not contact the passive electrode, and a retracted position in which the active electrode contacts the passive electrode.

The medical device may include one or more of the following features. When the active electrode is energized in the extended position, the passive electrode may be insulated, and when the active electrode is energized in the retracted position, the passive electrode may be energized. The passive electrode may include a substantially cylindrical shape with a flat distal end face and at least one rounded distal edge. The medical device may further include an outer insulating member surrounding at least a portion of the passive electrode. The medical device may further include an inner insulating member within the central opening between the active electrode and the passive electrode.

The medical device may further include a handle with a main part and a movable part, and at least one of the main part and the movable part may include a slot, such that in response to sliding the movable part in a first direction relative to the main part the active electrode is extendable, and in response to sliding the movable part in a second direction relative to the main part the active electrode is retractable. At least one of the main part and the movable part may include a fluid port to couple a fluid source to the handle, and at least one of the main part and the movable part may include a hub to couple an energy source to the handle. The medical device may further include a drive element, and the drive element may extend from the handle to the active electrode to electrically connect the energy source to the active electrode, and to move the active electrode distally or proximally based on relative movement between the main part and the movable part.

An entire distalmost face of the passive electrode may be conductive. The active electrode may include a distal tip and a longitudinal shaft. In a retracted position, only a proximal surface of the distal tip of the active electrode may contact the passive electrode. The distal tip may include a width that is greater than a width of the longitudinal shaft, as measured transverse to a longitudinal axis of the medical device. The distal tip may include a width that is greater than a diameter of the central opening, as measured transverse to a longitudinal axis of the medical device. The shaft may include a central lumen configured to direct a flow of fluid through the shaft, and the active electrode may include an electrode lumen in fluid communication with the central lumen. The electrode lumen may be configured to receive the flow of fluid from the central lumen and direct the fluid distally through an opening. The distal end may include a cap having a narrowed stop surface radially surrounding a portion of the active electrode, and the active electrode may include a widened portion proximal to a distal tip of the active electrode. The stop surface of the cap and the widened portion of the active electrode may limit a distal extension of the active electrode. The medical device may further include an insulating member radially internal of the narrowed stop surface of the cap.

In another aspect, a medical device may include a shaft including a distal end cap that includes a conductive portion, a movable electrode positioned within and movable relative to the distal end cap, where the movable electrode is configured to receive energy from an energy source, and a control element configured to control the position of the movable electrode between at least a retracted position and an extended position. In the retracted position, the movable electrode may be in electrical contact with the conductive portion, and, in the extended position, the movable electrode may be electrically insulated from the conductive portion.

The medical device may include one or more of the following features. The medical device may further include a fluid source coupled to the shaft. The shaft may include a shaft lumen fluidly connected to the fluid source, and the movable electrode may include an electrode lumen fluidly connected to the shaft lumen. The medical device may further include the energy source. The energy source may be an RF generator. The movable electrode may be movable through a central opening in the distal end cap such that the conductive portion radially surrounds the movable electrode.

In a further aspect, a method of treating tissue may include inserting a distal portion of a medical device into a body cavity, where the medical device may include a movable electrode and a conductive portion at the distal portion, extending the movable electrode distally such that the movable electrode is electrically isolated from the conductive portion, energizing the movable electrode, applying the movable electrode to a treatment site in the body cavity to deliver electrical energy to the treatment site, retracting the movable electrode proximally such that the movable electrode is electrically connected to the conductive portion, and applying the movable electrode and the conductive portion to the treatment site or another portion of the body cavity to deliver electrical energy.

The method may include one or more of the following features. The medical device may further include a fluid lumen, and the movable electrode may include a fluid outlet. The method may further include contemporaneously delivering fluid and applying electrical energy to the movable electrode.

It may be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

DETAILED DESCRIPTION

Examples of the present disclosure include devices and methods for: facilitating and improving the efficacy, efficiency, and/or safety of treating tissue when, for example, applying electrical energy to tissue; and, in certain embodiments, delivering fluid into and/or under tissue during a medical procedure. For example, aspects of the present disclosure may provide a user (e.g., physician, medical technician, or other medical service provider) with the ability to apply electrical energy or heat to tissue using a medical device having an electrode, and to deliver fluid into and/or under tissue with the same medical device. Additionally, aspects of the present disclosure may provide the user with the ability to use the medical device to deliver energy to tissue with the electrode to resect, cut, dissect, ablate, mark, or otherwise treat the tissue. Aspects of the present disclosure may also provide the user with the ability to then use the medical device to deliver energy to tissue with a larger electrode surface area to coagulate, cauterize, or otherwise treat the tissue in a hemostasis procedure, without removing the medical device from the treatment site. Furthermore, aspects of the present disclosure may provide the user with the ability to use the medical device to deliver fluid to the treatment site, without removing the medical device from the treatment site. Some aspects of the present disclosure may be used in performing an endoscopic, laparoscopic, arthroscopic, or other type of procedure.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device. When used herein, "proximal" refers to a position relatively closer to the exterior of the body or closer to a medical professional using the medical device. In contrast, "distal" refers to a position relatively further away from the medical professional using the medical device, or closer to the interior of the body. As used herein, the terms "comprises," "comprising," "having," "including," or other variations thereof, are intended to cover a non-exclusive inclusion, such that a device or method that comprises a list of elements does not include only those elements, but may include other elements not expressly listed or inherent thereto. Unless stated otherwise, the term "exemplary" is used in the sense of "example" rather than "ideal." As used herein, the terms "about," "substantially," and "approximately," indicate a range of values within +/−10% of a stated value.

Figures 1A, 1B:
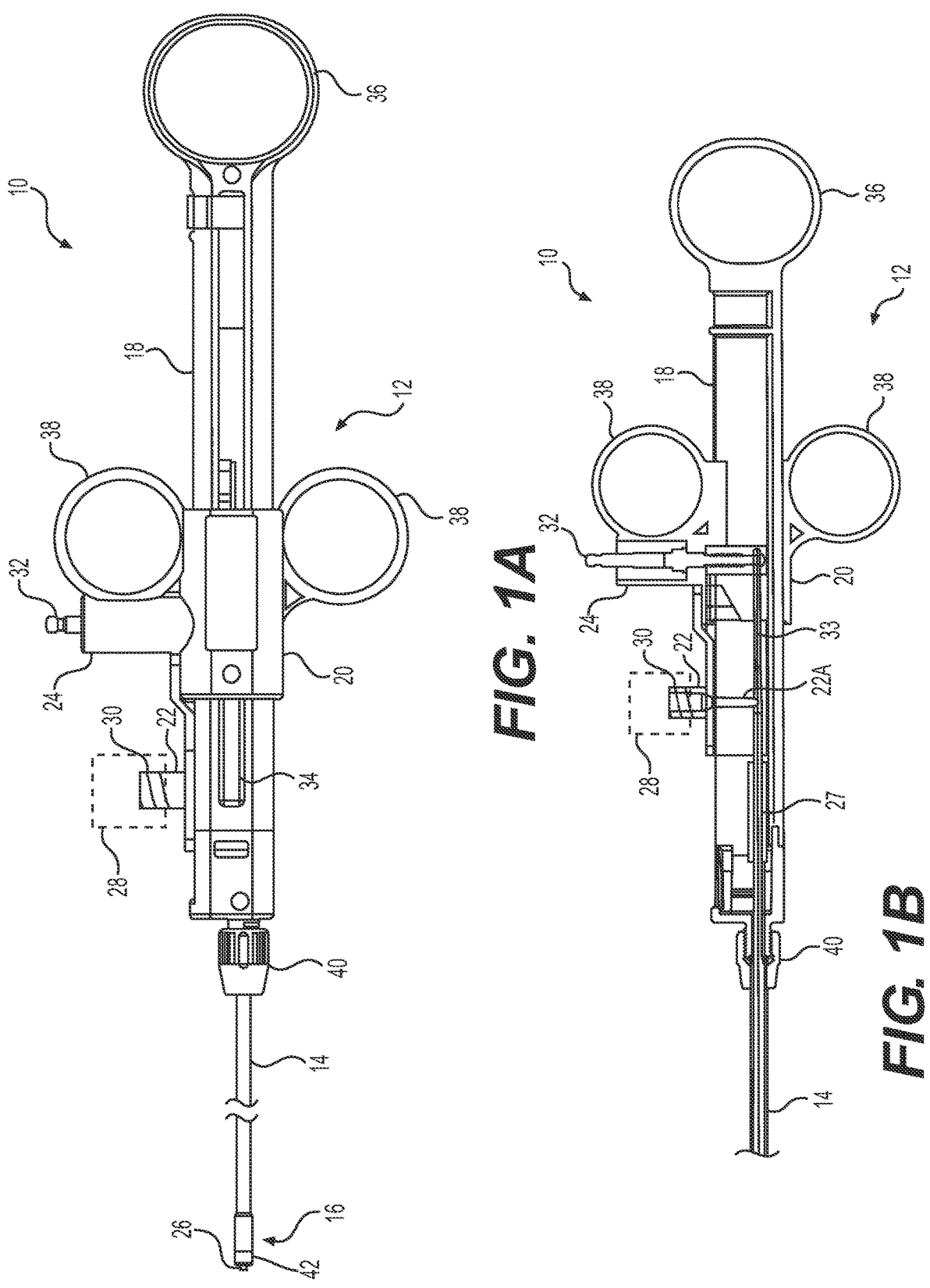
FIGS. 1A and 1B illustrate an exemplary medical device, according to aspects of this disclosure.

FIGS. 1A and 1B depict a medical device 10 that includes a handle 12, a shaft 14, and a distal end 16. Handle 12 may include a main body 18 and a movable body 20. Handle 12 also may include a port 22 configured to receive fluid, and a hub 24 configured to receive electrical energy similar to an electrical plug or socket. Distal end 16 includes an electrode 26 and an end cap 42. Electrode 26 is an active electrode that is electrically connected to hub 24, and includes one or more lumens (FIG. 3C) fluidly connected to port 22. As discussed in detail below, end cap 42 includes a passive conductive portion, which may be energized when in contact with electrode 26. Medical device 10 may be inserted into a body lumen of a subject, either through an insertion device (not shown) or alone, such that at least a portion of shaft 14 may be within the subject, while handle 12 may remain outside of the subject. From outside of the subject, a user can manipulate handle 12. For example, movement of movable body 20 relative to main body 18 in a first direction may extend electrode 26 relative to shaft 14 (e.g., move electrode 26 distally relative to a distal end of shaft 14 and end cap 42), while movement of movable body 20 relative to main body 18 in a second direction may retract electrode 26 relative to shaft 14 (e.g., move electrode 26 proximally relative to a distal end of shaft 14 and end cap 42).

Handle 12 may be coupled to a fluid source via port 22. Port 22 may be fluidly coupled to electrode 26 via an internal lumen 27 through shaft 14. For example, as shown in FIG. 1B, internal lumen 27 may extend longitudinally through main body 18 of handle 12, and port 22 may include a port lumen 22A that extends through port 22 to fluidly connect port 22 to internal lumen 27. The fluid source may include an irrigation bag, vial, syringe, or other container or reservoir of a saline solution or other fluid. The fluid source may pressurize the fluid via a pump, an injection needle, a gravity drip, or other pressure source. The fluid source may be user controlled via a trigger, foot pedal, adjustable dial, or other control device, and/or may deliver an automatic or constant irrigation supply. Port 22 may be positioned on a distal portion of main body 18 or on movable body 20. Moreover, port 22 may include a one-way valve 28, a luer, a seal, threading 30, or any appropriate element to maintain a secure connection between handle 12 and the fluid source, minimize or prevent back-flow (e.g., fluid flowing proximally out of port 22), and/or minimize or prevent leakage. In one example, one-way valve 28 may include an outer housing containing an inner elastomeric and/or gelatinous sealing member (not shown).

Handle 12 may be coupled to an energy source through hub 24. Hub 24 may be electrically coupled to electrode 26 via a conductive element in shaft 14. The energy source may be an electrocautery source, an RF generator, a heating source, a current generator, etc. In one aspect, medical device 10 may be used for a monopolar electrosurgery procedure, and may include a return electrode positioned remotely from electrode 26. Alternatively, medical device 10 may be used for a bipolar electrosurgery procedure. As discussed with the fluid source, the energy source may include any control element to allow a user to control the delivery of the energy. Hub 24 may be positioned on movable body 20 or on main body, and may include one or more pins or prongs 32 to couple to the energy source. In one aspect shown in FIG. 1B, prong 32 may extend through hub 24 transverse to a longitudinal axis of handle 12, and may be electrically and physically connected to a conductive element 33, such as a wire, a cable, and/or a braided sheath. Conductive element 33 may be electrically conductive or include an electrically conductive element, and conductive element 33 may extend longitudinally through internal lumen 27 and through shaft 14. As shown in FIG. 1B, fluid delivered through port 22 may surround at least a portion of conductive element 33. In another aspect, the energy source may be a part of handle 12.

As mentioned, handle 12 may control the extension or retraction of electrode 26 relative to the distal end 16 of shaft 14 and end cap 42. For example, main body 18 may include a slot 34 and a thumb ring 36. Movable body 20 may be slidably positioned within slot 34 and include one or more finger holes 38. Movable body 20 may be coupled to a drive element, and the drive element may impart distal or proximal movement to at least a portion of electrode 26 based on relative movement between main body 18 and movable body 20. In one aspect, conductive element 33 may also be a drive wire, rod, cable, or the like, such that conductive element 33 imparts distal or proximal movement to at least a portion of electrode 26 while also coupling electrode 26 to hub 24, e.g., the one or more prongs 32, to deliver the energy to electrode 26. Although not shown, handle 12 may also include a locking mechanism to selectively secure movable body 20 at a predetermined position along slot 34, and/or within a predetermined range of positions along slot 34, to releasably fix the relative positions of main body 18 and movable body 20, and, thus, of electrode 26 and shaft 14.

Shaft 14 extends from a distal portion of main body 18 to distal end 16, and may surround at least a portion of electrode 26. Shaft 14 may be coupled to handle 12 via a coupler 40, which may surround a portion of shaft 14 and screw onto main body 18 to secure the elements. Shaft 14 may be a sheath that surrounds at least a portion of the central lumen and the drive wire. In another aspect, shaft 14 may be an extrusion that includes one or more lumens extending from handle 12 to distal end 16. In either aspect, shaft 14 may electrically insulate and fluidly isolate the elements positioned within shaft 14 in order to protect the user and the subject.

Figure 2A:
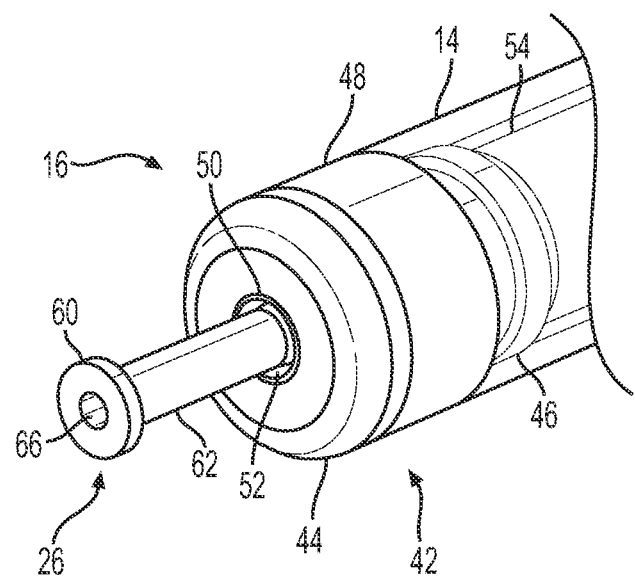
FIGS. 2A and 2B illustrate perspective views of a distal portion of the medical device of FIGS. 1A and 1B in extended and retracted configurations, according to aspects of the present disclosure.
Figure 2B:
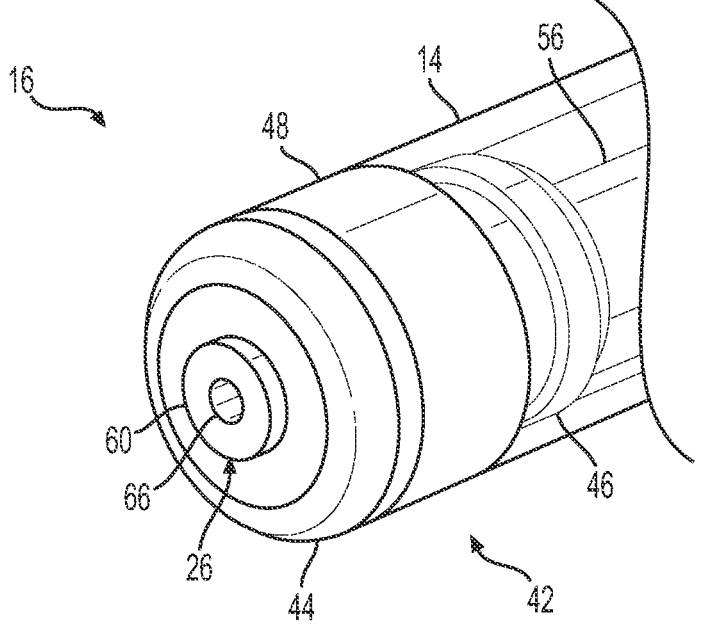

FIGS. 2A and 2B illustrate additional aspects of distal end 16. It is noted that FIGS. 2A and 2B illustrate a portion of shaft 14 being transparent in order to show the internal components of distal end 16.

FIGS. 2A and 2B show perspective views of a portion of distal end 16, with a portion of electrode 26 positioned within end cap 42 of distal end 16. End cap 42 may include a distal end portion 44 and one or more internal portions 46. End cap 42 may be a separate component coupled to shaft 14 or may be integrally formed with shaft 14. Although not shown, internal portions 46 may include a one or more graduated surfaces of different radii or sizes, which may aid in the coupling of end cap 42 to shaft 14. In one aspect, distal end portion 44 is electrically conductive, and the one or more internal portions 46 are at least partially electrically insulating. For example, distal end portion 44 may be formed of a metallic or other conductive material, and internal portions 46 may be of a ceramic material or another non-conductive material. In another aspect, distal end portion 44 may include a metallic or conductive coating on the exterior of a ceramic material or other non-conductive material. Distal end portion 44 may be a passive electrode without a dedicated conductive element. For instance, with electrode 26 energized and extended as discussed above, electrode 26 does not contact distal end portion 44, and distal end portion 44 is not energized. However, when electrode 26 is energized and retracted, electrode 26 contacts distal end portion 44, and distal end portion 44 is energized. As shown, distal end portion 44 may include a substantially cylindrical shape, with a flat distal end face, and rounded distal edges. In one aspect, the entire distal-facing surface of end cap 42 is conductive. End cap 42 and distal end portion 44 also include a central opening 52, as discussed below.

End cap 42 may include an outer insulating member 48, which may radially surround a portion of distal end portion 44. End cap 42 may also include an inner insulating member 50. Inner insulating member 50 may be positioned radially within end cap 42, for example, radially within distal end portion 44 and surround central opening 52, in order to at least partially insulate distal end portion 44 from a portion of electrode 26 positioned within central opening 52. Outer insulating member 48 and inner insulating member 50 may each be formed of a ceramic material, an elastomeric polymer material, or another non-conductive material.

Moreover, as shown in FIG. 2A, end cap 42 includes central opening 52 through which electrode 26 may be positioned. Central opening 52 may be larger than electrode 26 (e.g., have a larger diameter) in order to form a gap between distal end portion 44, inner insulating member 50, and electrode 26. The gap formed by central opening 52 may help to electrically insulate distal end portion 44 from electrode 26 when electrode 26 is in an extended position.

Electrode 26 may be coupled to a proximal support 54 of distal end 16, which includes a cylindrical extension 56. Proximal support 54 may be coupled to a portion of, may extend distally of, and may receive at least a portion of, electrode 26 in order to partially overlap. Electrode 26 and cylindrical extension 56 may be coupled via welding, an adhesive, crimping, friction fit, or other appropriate coupling. Electrode 26 and proximal support 54 may be movable relative to end cap 42 in response to the relative movement of movable body 20 and main body 18 of handle 12. For example, with movable body 20 in a proximal position relative to main body 18, electrode 26 may be substantially retracted within end cap 42 with only a distal portion (e.g., a distal tip 60) of electrode 26 extending distally beyond end cap 42 (FIG. 2B). In the retracted position shown in FIG. 2B, a portion of electrode 26 is in contact with and electrically connected to distal end portion 44. Then, as movable body 20 is translated distally relative to main body 18, electrode 26 and proximal support 54 translate distally relative to end cap 42 such that a greater portion of electrode 26 extends distally beyond end cap 42 through central opening 52 (FIG. 2A).

Electrode 26 includes a distal tip 60 and a longitudinal portion 62. Distal tip 60 may be wider than longitudinal portion 62, and distal tip 60 may be wider than central opening 52 through end cap 42, as discussed above, with the width being measured transverse to a longitudinal axis of longitudinal portion 62 and medical device 10. As shown in FIG. 3C, electrode 26 also includes an electrode lumen 64 extending through longitudinal portion 62. Electrode lumen 64 is in fluid communication with port 22 via at least one lumen 70 through proximal support 54. In one aspect, an inner sheath 41 may form at least a portion of the fluid connection between lumen 70 and port 22. Additionally, electrode lumen 64 is in fluid communication with an outlet 66 within distal tip 60 that allows fluid to flow from electrode lumen 64. In one aspect, outlet 66 is circular and is centrally located on the distalmost face of distal tip 60.

Although not shown, electrode 26 may include any number of outlets 66, and outlets 66 may be arranged in any position and in any direction on electrode 26 in order to deliver fluid to the body cavity. Furthermore, while this disclosure discusses the contact between electrode 26 and distal end portion 44 being formed by a proximal portion (e.g., a proximalmost face) of distal tip 60 contacting the distal end face of distal end portion 44, this disclosure is not so limited. For example, in one aspect, longitudinal portion 62 of electrode 26 may have a radial extension configured to extend through an opening in inner insulating member 50 or otherwise electrically connect electrode 26 and distal end portion 44 when electrode 26 is retracted.

Figure 3A:
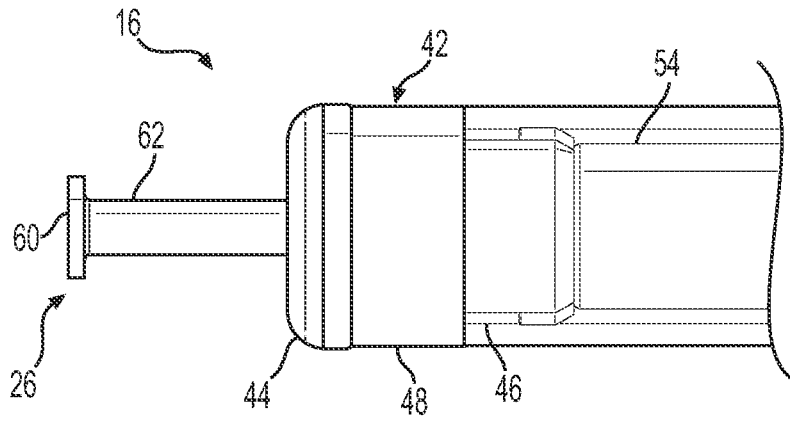
FIGS. 3A and 3B illustrate side views of the distal portion of the medical device of FIGS. 1A and 1B in extended and retracted configurations, according to aspects of the present disclosure.
Figure 3B:
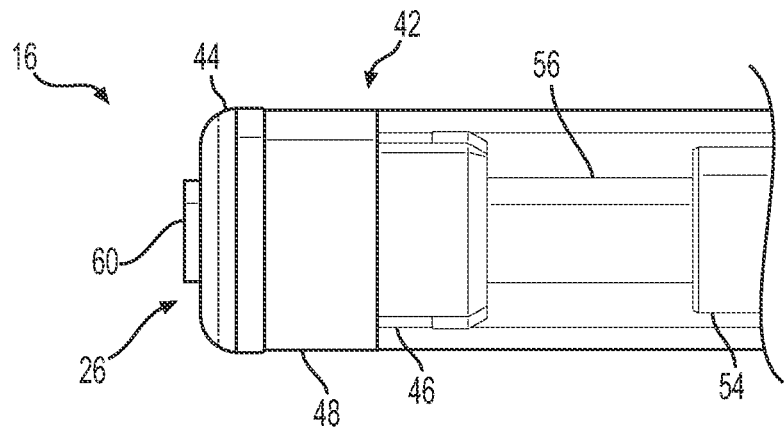
Figure 3C:
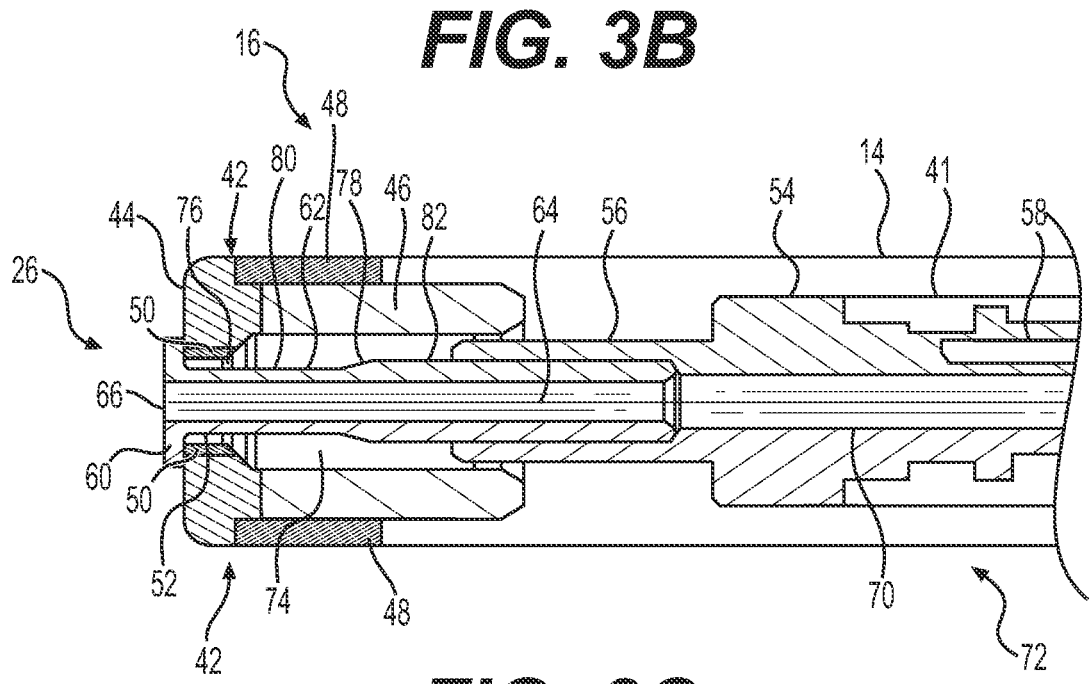
FIG. 3C illustrates a cross-sectional view of the distal portion of the medical device of FIGS. 1A and 1B in a retracted position, according to aspects of the present disclosure.

FIGS. 3A and 3B illustrate side views of a portion of distal end 16, and FIG. 3C illustrates a cross-sectional view of a portion of distal end 16. Again, it is noted that FIGS. 3A and 3B illustrate a portion of shaft 14 being transparent in order to show the internal components of distal end 16.

As shown in FIGS. 3A and 3B, electrode 26 may include an extended configuration (FIG. 3A) and a retracted configuration (FIG. 3B). In the extended configuration, distal tip 60 extends distally beyond distal end portion 44. In the retracted configuration, a portion of distal tip 60 (e.g., an annular proximalmost surface) abuts and is electrically connected to distal end portion 44. Moreover, it is noted that the relative sizes of electrode proximal support 54 and internal portions 46 of end cap 42 may limit the distal extension of electrode 26 (FIG. 3A).

Electrode 26 includes a shape with distal tip 60 being wider than longitudinal portion 62, as measured transverse to the longitudinal axis of medical device 10. For example, electrode 26 may include a substantially T-shaped cross-sectional profile. Electrode 16 may also include different shapes. In either aspect, distal tip 60 may contact distal end portion 44 in the retracted position such that, when electrode 26 is in the retracted configuration and is energized, distal end portion 44 is also energized. On the other hand, when electrode 26 is in the extended configuration and is energized, the gap formed by central opening 52, along with inner insulating member 50, prevents distal end portion 44 from also being energized.

FIG. 3C illustrates the cross-sectional profile of distal portion 16. As shown, electrode 26 may be proximally supported by proximal support 54. Proximal support 54 may include a drive wire receiving portion 58. Drive wire receiving portion 58 may be an indentation or recess that extends parallel to at least a portion of lumen 70. Drive wire receiving portion 58 may receive a portion of a drive wire (e.g., wire 33), and the drive wire and/or inner sheath 41 may be coupled to movable body 20 such that the movement of movable body 20 imparts distal or proximal movement to proximal support 54 and, thus, to electrode 26. The drive wire may be coupled to drive wire receiving portion 58 within coupling portion 72 by welding, an adhesive, crimping, friction fit, or any other permanent or temporary coupling. Proximal support 54 may also be coupled to electrode 26 by welding, an adhesive, crimping, friction fit, or any other permanent or temporary coupling. In one aspect, both the drive wire and proximal support 54 are conductive to electrically connect the one or more prongs 32 of hub 24 to electrode 26. In another aspect, proximal support 54 may be at least partially insulating, and may include a wire or other conductive element electrically connecting the drive wire to electrode 26. Similarly, in one aspect, the drive wire may be at least partially insulating and may include a wire or other conductive element. Furthermore, at least a portion of the drive wire may be positioned within inner sheath 41. Alternatively, the drive wire may be positioned within a separate lumen in shaft 14 (e.g., a lumen separate from the lumen extending through inner sheath 41).

End cap 42 includes a central lumen 74 through which electrode 26 may move during the extension and retraction. End cap 42 may also include a narrowing portion or stop surface 76 at a distal end of central lumen 74. Electrode 26 may include a widened portion 78 between a first longitudinal portion 80 and a second longitudinal portion 82 of longitudinal portion 62. A diameter of at least a portion of widened portion 78 is larger than a diameter of stop surface 76. Stop surface 76 and widened portion 78 may limit the distal extension of electrode 26 through end cap 42. Moreover, inner insulating member 50 may extend proximally to stop surface 76 in order to insulate distal end portion 44 from electrode 26 when electrode 26 is in the extended position. Additionally, although not shown, end cap 42 may be fixedly coupled to shaft 14 via welding, an adhesive, crimping, friction fit, or other appropriate coupling.

With electrode 26 in an extended position (FIG. 2A), first longitudinal portion 80 of electrode 26 may protrude from end cap 42 and may form an exposed portion. Electrode 26 may be energized, and the exposed portion may be used for resecting, cutting, dissecting, ablating, marking, or otherwise treating the tissue. With electrode 26 in a retracted position (FIG. 2B) and energized such that both electrode 26 and distal end portion 44 are energized, distal tip 60 and distal end portion 44 may form a larger energized portion of medical device 10 that may be used to coagulate, cauterize, or otherwise treat the tissue. For example, electrode 26 may be extended and energized in order to perform an accurate resecting or marking procedure. The size and shape of electrode 26 may help to decrease the risk of energy being delivered to unintended portions of the tissue. For example, distal tip 60 may include an outer diameter of approximately 0.8 mm, as measured transverse to a longitudinal axis of medical device 10, and electrode outlet 66 may include a diameter of approximately 0.3 mm, as measured transverse to the longitudinal axis of medical device 10. Additionally, electrode 26 may be retracted and energized to perform a hemostasis procedure. The size of the energized portion formed by distal tip 60 and distal end portion 44 may be equal to or larger than a diameter of a vessel in the tissue being treated. In one aspect, distal end portion 44 may include a major diameter (e.g., extending from opposite sides of the radial exterior) of approximately 1.55 mm, as measured transverse to the longitudinal axis of medical device 10, and may include a minor diameter (e.g., extending from opposite sides of the distal end face) of approximately 0.75 mm, as measured transverse to the longitudinal axis of medical device 10. Central opening 52 may include a diameter that is slightly larger than the diameter of longitudinal portion 62 of electrode 26, but may also be slightly smaller than the diameter of distal tip 60. In this aspect, distal end portion 44 may include a surface area (e.g., the distal end face of distal end portion 44) of approximately 1.44 mm². Moreover, end cap 42 may include a diameter of approximately 2.2 mm, as measured transverse to the longitudinal axis of medical device 10. Accordingly, medical device 10 may be used to perform a resection procedure and a hemostasis procedure without removing medical device 10 from the body cavity, reducing procedure time and minimizing risks to the subject.

Additionally, medical device 10 may be used to deliver fluid to the body cavity. For example, medical device 10 may inject a fluid through outlet 66 into a submucosal plane of the treatment site, which may help provide a bleb or cushion below the tissue being treated. The fluid may be injected before, during, or after resection or hemostasis procedures, and does not require any exchange of devices.

Figure 4:
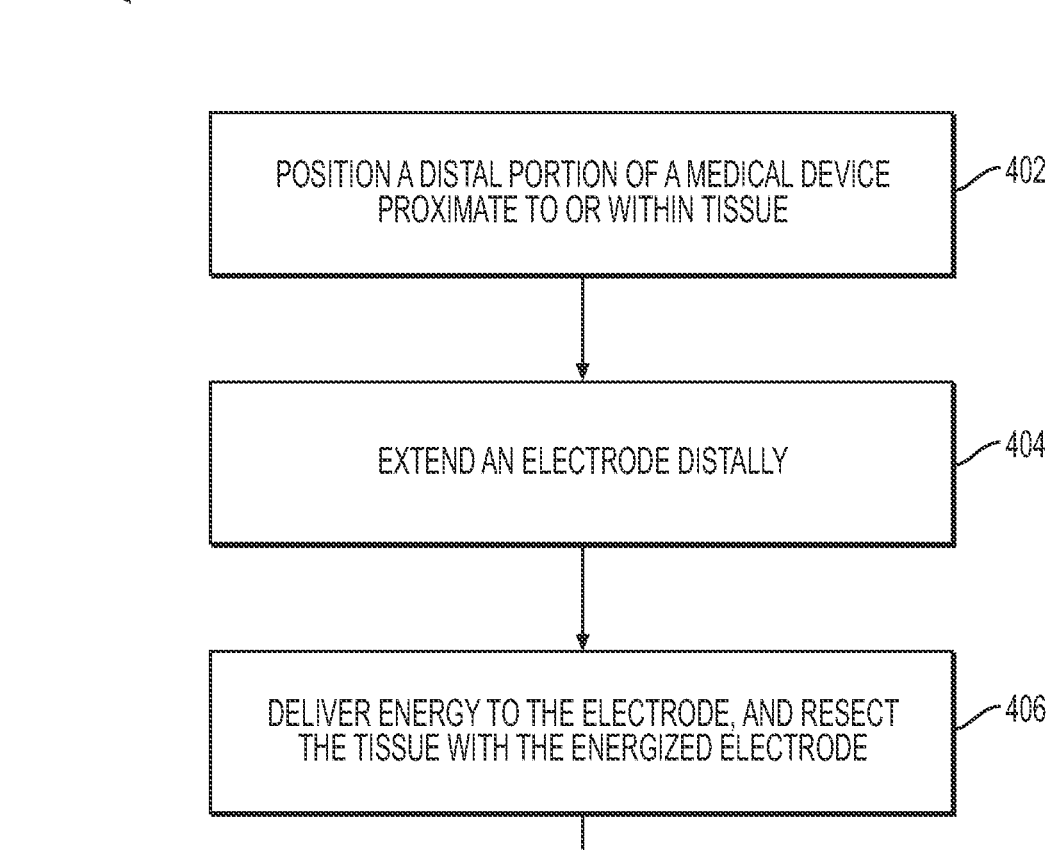
FIG. 4 is a flow diagram of an exemplary tissue treatment method, according to aspects of the present disclosure.

FIG. 4 is a flow diagram portraying an exemplary tissue treatment method 400 to apply energy for at least one tissue resection or cautery procedure. Method 400 includes a step 402, wherein the user positions a distal portion of the medical device proximate or within tissue. Step 402 may include a preliminary step of injecting a fluid into the tissue with a separate conventional needle injector or through outlet 66. The preliminary injection may separate or expand one or more layers of tissue, beneath or containing a diseased portion of tissue, to lift the diseased tissue away from underlying layers of tissue, thereby creating a tissue bleb. Step 402 may also include delivering the medical device through an insertion device.

In a step 404, the user may extend the electrode distally from the distal portion of the medical device. For example, the medical device may be delivered to the tissue through the insertion device with the electrode proximally retracted. Step 404 may include extending electrode 26 by action on movable body 20 of handle 12 relative to main body 18, as discussed above.

In a step 406, the user may deliver energy to the electrode, and may apply the energized electrode to the tissue in order to resect, cut, dissect, ablate, mark, or otherwise treat the tissue. Additionally, the energy may be delivered to electrode 26 from an energy source, which may be controlled by a user interface.

In a step 408, the user may retract the electrode proximally toward the distal portion of the medical device. For example, step 408 may include retracting electrode 26 by action of movable body 20 of handle 12 relative to main body 18, as discussed above. In step 408, electrode 26 may be retracted such that one or more portions of distal tip 60 contact distal end portion 44. As a result, any energy delivered to electrode 26 also energizes distal end portion 44, dispersing the delivered energy and enlarging the energized portion of medical device 10. The larger energized portion, formed by electrode 26 and distal end portion 44, may be larger than a vessel in the tissue being treated.

Then, method 400 may include a step 410, in which the user may again deliver energy to the electrode. With electrode 26 in the retracted position, the energy is delivered through electrode 26 and distal end portion 44. Electrode 26 and distal end portion 44 may be applied to tissue to coagulate, cauterize, or otherwise treat the tissue.

In one aspect, a user may extend electrode 26 and deliver energy to electrode 26 (with distal end portion 44 being isolated) to accurately resect tissue with a reduced risk of thermal perforation to the surrounding area of the body cavity. When hemostasis is needed, the user may retract electrode 26 proximally such that a portion of electrode 26 (e.g., distal tip 60) contacts distal end portion 44, thereby energizing the previously non-energized distal end portion 44. With both electrode 26 and distal end portion 44 energized, medical device 10 provides a greater energized surface area, which, in turn, may allow for more effective hemostasis. For example, the surface area of distal tip 60 and distal end portion 44 may be larger than a blood vessel that is in need of hemostasis, and thus may more effectively cauterize or coagulate a bleed than if only electrode 26 was energized and applied to the tissue.

Based on the type of medical procedure and progress of the tissue treatment, the user may repeat the steps of method 400 as many times as necessary to perform the tissue treatment procedure. For example, the user may cycle back from step 410 to step 402. The user may extend and retract electrode 26 in order to alternate between resection and coagulation procedures. The user may also reposition distal end 16 and perform method 400 as many times as necessary in order to perform the tissue treatment procedure. Additionally, during any of the aforementioned steps, a user may deliver fluid to the tissue. The fluid may be delivered from a fluid source, through port 22, port lumen 22A, internal lumen 27, support lumen 70, and electrode lumen 64 to one or more outlets 66 in electrode 26. For example, delivering fluid may form, re-form, maintain, and/or enlarge a bleb in the tissue. The delivery of the energy and fluid discussed in method 400 may be performed contemporaneous or may be staggered depending on the medical procedure. Moreover, medical device 10 may be used to perform any of the above procedures, without the need to remove or replace medical device 10 from the body cavity, which may reduce the overall procedure time and/or reduce the risks to the subject.

While principles of the present disclosure are described herein with reference to illustrative aspects for particular applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the disclosure is not to be considered as limited by the foregoing description.

We claim:

1. A medical device, comprising:
a handle with a main part and a movable part, wherein at least one of the main part or the movable part includes a hub to couple an energy source to the handle;
a shaft including a shaft lumen and a distal end, wherein the distal end includes a passive electrode;
an active electrode, wherein the active electrode includes an electrode lumen in fluid communication with an outlet at a distal tip to deliver fluid; and
a proximal support coupled to and partially overlapping with the active electrode, wherein the proximal support includes a proximal support lumen that fluidly couples the shaft lumen to the electrode lumen, wherein the proximal support includes a receiving lumen that extends parallel to a portion of the proximal support lumen, and wherein the receiving lumen is configured to receive a portion of a drive element, such that the proximal support is configured to electrically connect the drive element to the active electrode,
wherein movement of the proximal support controls a position of the active electrode relative to the passive electrode.

2. The medical device of claim 1, wherein at least one of the main part or the movable part of the handle includes a fluid port to couple a fluid source to the handle.

3. The medical device of claim 1, wherein the passive electrode defines a central opening extending through the passive electrode, wherein the active electrode is movably positioned within the central opening, and wherein the medical device further comprises an inner insulating member within the central opening between the active electrode and the passive electrode.

4. The medical device of claim 3, further comprising an outer insulating member surrounding at least a portion of the passive electrode.

5. The medical device of claim 1, wherein the active electrode is movable between at least:
an extended position in which the active electrode does not contact the passive electrode, and
a retracted position in which the active electrode contacts the passive electrode.

6. The medical device of claim 5, wherein the proximal support lumen fluidly couples the shaft lumen to the electrode lumen both when the active electrode is in the extended position and when the active electrode is in the retracted position.

7. The medical device of claim 5, wherein, when the active electrode is energized in the extended position, the passive electrode is not energized, and
wherein, when the active electrode is energized in the retracted position, the passive electrode is energized.

8. The medical device of claim 5, wherein the passive electrode includes a central opening,
wherein an entire distalmost face of the passive electrode is conductive,
wherein the active electrode includes the distal tip and a longitudinal shaft, wherein the distal tip includes a width that is greater than both a width of the longitudinal shaft and a diameter of the central opening, as measured transverse to a longitudinal axis of the medical device, and
wherein, in the retracted position, only a proximal surface of the distal tip of the active electrode contacts the passive electrode.

9. The medical device of claim 1, further comprising:
the drive element, wherein the drive element extends from the handle to the proximal support to electrically connect the energy source to the active electrode, and to move the active electrode distally or proximally based on relative movement between the main part and the movable part.

10. The medical device of claim 9, wherein at least one of the main part or the movable part includes a slot, such that in response to sliding the movable part in a first direction relative to the main part the active electrode is extendable, and in response to sliding the movable part in a second direction relative to the main part the active electrode is retractable.

11. A medical device, comprising:
a handle with a main part and a movable part, wherein at least one of the main part or the movable part includes a hub to couple an energy source to the handle;
a shaft including a shaft lumen and a distal end, wherein the distal end includes a passive electrode that defines an opening extending through the passive electrode;
an active electrode movable relative to the passive electrode through the opening, wherein the active electrode includes an electrode lumen in fluid communication with an outlet at a distal tip to deliver fluid, and wherein the distal tip of the active electrode includes a width that is greater than a width of the opening, as measured transverse to a longitudinal axis of the medical device; and
a proximal support coupled to and partially overlapping with the active electrode, wherein the proximal support includes:
a proximal support lumen that fluidly couples the shaft lumen to the electrode lumen, and
a receiving lumen that extends parallel to a portion of the proximal support lumen,
wherein the receiving lumen is configured to receive a portion of a drive element, such that the proximal support electrically connects the drive element to the active electrode,
wherein movement of the movable part of the handle controls a position of the proximal support relative to the shaft, and also controls a position of the active electrode relative to the passive electrode between at least an extended position and a retracted position.

12. The medical device of claim 11, wherein the distal end includes a narrowed stop surface radially surrounding a portion of the active electrode, wherein the active electrode includes a widened portion proximal to a distal tip of the active electrode, wherein the narrowed stop surface of the distal end and the widened portion of the active electrode limit a distal extension of the active electrode.

13. The medical device of claim 12, wherein the medical device further comprises an insulating member radially internal of the narrowed stop surface of the distal end.

14. The medical device of claim 11, wherein, in the retracted position, only a proximal surface of the distal tip of the active electrode contacts the passive electrode.

15. A medical device, comprising:
a handle with a main part and a movable part, wherein at least one of the main part or the movable part includes a hub to couple an energy source to the handle;
a shaft including a shaft lumen and a distal end, wherein the distal end includes a passive electrode that defines a central opening extending through the passive electrode;

an active electrode movable within the central opening, wherein the active electrode includes an electrode lumen in fluid communication with an outlet at a distal tip to deliver fluid, and wherein the distal tip of the active electrode includes a width that is greater than a width of the central opening as measured transverse to a longitudinal axis of the medical device;

a proximal support coupled to and partially overlapping with the active electrode, wherein the proximal support includes:

a proximal support lumen that fluidly couples the shaft lumen to the electrode lumen; and a receiving lumen that extends parallel to a portion of the proximal support lumen, wherein the receiving lumen is configured to receive a portion of a drive element, such that the proximal support electrically connects the drive element to the active electrode; and the drive element, wherein the drive element extends from the handle to the proximal support to electrically connect the energy source to the active electrode, and to move the proximal support and the active electrode distally or proximally based on the relative movement between the main part and the movable part, wherein movement of the movable part of the handle controls a position of the proximal support relative to the shaft, and also controls a position of the active electrode relative to the passive electrode between at least an extended position and a retracted position.

16. The medical device of claim 15, wherein at least one of the main part or the movable part of the handle includes a fluid port to couple a fluid source to the handle.

17. The medical device of claim 15, further comprising:

an inner insulating member within the central opening between the active electrode and the passive electrode; and an outer insulating member surrounding at least a portion of the passive electrode.

18. The medical device of claim 17, wherein an entire distalmost face of the passive electrode is conductive, wherein the active electrode includes the distal tip and a longitudinal shaft, wherein the distal tip includes a width that is greater than both a width of the longitudinal shaft and a diameter of the central opening, as measured transverse to the longitudinal axis of the medical device, and wherein, in the retracted position, only a proximal surface of the distal tip of the active electrode contacts the passive electrode.

* * * * *